US008447373B2

(12) United States Patent
Boppart (10) Patent No.: US 8,447,373 B2
(45) Date of Patent: May 21, 2013

(54) APPARATUS AND METHOD FOR MEASURING A CHARACTERISTIC OF A COMPOSITION REACTIVE TO A MAGNETIC FIELD

(75) Inventor: Stephen A. Boppart, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 974 days.

(21) Appl. No.: 12/464,020

(22) Filed: May 11, 2009

(65) Prior Publication Data
US 2009/0306489 A1      Dec. 10, 2009

Related U.S. Application Data

(60) Provisional application No. 61/060,013, filed on Jun. 9, 2008.

(51) Int. Cl.
*A61B 5/00* (2006.01)
(52) U.S. Cl.
USPC ........................................................ 600/324
(58) Field of Classification Search
USPC ............... 600/9, 410, 309, 310, 322, 323, 328
See application file for complete search history.

(56) References Cited

U.S. PATENT DOCUMENTS

| 5,323,776 | A | 6/1994 | Blakeley et al. |
| 5,833,601 | A | 11/1998 | Swartz et al. |
| 2006/0264720 | A1 | 11/2006 | Chew et al. |
| 2007/0004957 | A1* | 1/2007 | Hilburg ............................. 600/9 |
| 2007/0073140 | A1* | 3/2007 | Fisher et al. .................. 600/410 |

FOREIGN PATENT DOCUMENTS

| JP | 1006753 | | 1/1989 |
| JP | 2003287523 | | 10/2003 |
| WO | 9639933 | A1 | 12/1996 |

OTHER PUBLICATIONS

Barker et al., "Principles of Pulse Oximetry Technology", Sep. 2002, http://oxymetry.org/pulseox/principles.htm.
Chien et al., "Blood Viscosity: Influence of Erythrocyte Aggregation", pp. 829-831, Aug. 18, 1967.
Chien et al., "Blood Viscosity: Influence of Erythrocyte Deformation", pp. 827-829, Aug. 18, 1967.
Higashi et al., "Orientation of Erythrocytes in a Strong Static Magnetic Field", American Society of Hematology, pp. 1328-1334. www.bloodjournal.org, web site last visited May 12, 2009.
Masaaki Iino, "Effects of a Homogeneous Magnetic Field on Erythrocyte Sedimentation and Aggregation", Wiley-Liss, Inc., Bioelectromagnetics 18, pp. 215-222, 1997.

(Continued)

*Primary Examiner* — Brian Szmal
(74) *Attorney, Agent, or Firm* — Guntin & Gust, PLC; Ed Guntin (57) ABSTRACT

A system that incorporates teachings of the present disclosure may include, for example, a sensor having a pulse oximeter sensor to measure an oxygen saturation level in a liquid, a magnetic source coupled to the pulse oximeter sensor, and a controller to control the pulse oximeter sensor and the magnetic source, and to measure a mechanical effect on the liquid responsive to the magnetic source applying a magnetic field to the liquid. Additional embodiments are disclosed.

32 Claims, 5 Drawing Sheets

OTHER PUBLICATIONS

Han et al., "Continuous Magnetophoretic Separation of Blood Cells in Microdevice Format", Journal of Applied Physics, vol. 96, pp. 5797-5802, Nov. 15, 2004.

R.S. Khandpur, "Biomedical Instrumentation: Technology and Applications", Chicago: McGraw-Hill 2005, pp. 318-322.

G.D.O. Lowe, "Blood Rheology in Vitro and in Vivo", in Bailliere's Clinical Haematology, Bailliere Tindall, Publisher. UK. Sep. 1987, vol. 1, No. 3. pp. 597-636.

Okazaki et al., "Effects of an Inhomogeneous Magnetic Field on Flowing Erythrocytes", European Biophysics Journal 14, pp. 139-145, 1987.

Shvartsman et al., Optical Transmission of Blood: Effect of Erythrocyte Aggregation, IEEE Transactions on Biomedical Engineering vol. 50, No. 8, pp. 1026-1033, Aug. 8, 2003.

Stuart et al., "Red Cell Deformability and Haematological Disorders", Longman Group UK Ltd., Blood Reviews (1990) 4, pp. 141-147.

Yamamoto et al., "A Blood-Oxygenation-Dependent Increase in Blood Viscosity Due to a Static Magnetic Field", Institute of Physics Publishing, Physics in Medicine and Biology, Phys.Med.Biol. 49, pp. 3267-3277, 2004.

\* cited by examiner

FIG. 7 700

APPARATUS AND METHOD FOR MEASURING A CHARACTERISTIC OF A COMPOSITION REACTIVE TO A MAGNETIC FIELD

PRIOR APPLICATION

The present application claims the priority of U.S. provisional patent application No. 61/060,013 filed Jun. 9, 2008. All sections of the aforementioned application are incorporated herein by reference.

FIELD OF THE DISCLOSURE

The present disclosure relates generally to measurements on compositions reactive to a magnetic field, and more specifically to an apparatus and method for measuring a characteristic of a composition reactive to a magnetic field.

BACKGROUND

Organic measurements can be used for monitoring or diagnosing the health of a human or animal patient. Organic measurements can take the form of invasive or non-invasive measurements. A typical invasive measurement procedure can involve the extraction of fluids or cells from a human or animal patient. Fluids such as blood can be used to diagnose the condition of the patient. Similarly, cells such as tissue can be used for biopsy analysis to detect disorders.

DETAILED DESCRIPTION

An embodiment of the present disclosure can entail a sensor having a pulse oximeter sensor to measure an oxygen saturation level in a liquid, a magnetic source coupled to the pulse oximeter sensor, and a controller to control the pulse oximeter sensor and the magnetic source, and measure a mechanical effect on the liquid responsive to the magnetic source applying a magnetic field to the liquid.

An embodiment of the present disclosure can entail a sensor having a pulse oximeter sensor for coupling to a magnetic source to measure a mechanical effect on a liquid carrying oxygen and one or more particles that kinetically react to magnetic fields.

An embodiment of the present disclosure can entail a device having a magnetic source for coupling to a pulse oximeter sensor to measure a mechanical effect on a liquid carrying oxygen and one or more particles that kinetically react to magnetic fields.

An embodiment of the present disclosure can entail a computing device having a controller for coupling to a magnetic source and a pulse oximeter sensor to control and measure a mechanical effect on a liquid carrying oxygen and one or more particles that kinetically react to magnetic fields.

An embodiment of the present disclosure can entail applying a magnetic field on a liquid carrying oxygen and one or more particles that kinetically react to magnetic fields, and measuring a mechanical effect on at least a portion of the liquid according to a change in an oxygen saturation level of said portion of the liquid.

An embodiment of the present disclosure can entail a computer-readable storage medium having computer instructions to perform a physiological diagnosis from a mechanical effect on a liquid carried by a patient affected by a magnetic field, wherein the liquid comprises oxygen and one or more particles that kinetically react to magnetic fields.

An embodiment of the present disclosure can entail applying a magnetic field on a plurality of biological cells carrying oxygen and one or more particles that kinetically react to magnetic fields, and measuring a mechanical effect from the application of the magnetic field on at least a portion of the plurality of biological cells according to a change in an oxygen saturation level of said portion of the plurality of biological cells.

An embodiment of the present disclosure can entail non-invasively applying a magnetic field on a living organism, and non-invasively measuring changes from the application of the magnetic field in at least one of an absorption and scattering of a select spectrum of light applied on the living organism.

The importance of individual medical exams providing both accurate and multiple amounts of patient information remains an important factor in future medicine. For instance, the Complete Blood Count (CBC) gives an array of information regarding the components of a patient's blood, and can help in the diagnosis of certain diseases. Despite the CBC providing detailed analysis of a patient's health, it displays a problem evident in many medical exams today; they are invasive.

An invasive medical exam requires a patient to undergo an incision (as in exploratory surgery) or insertion of a medical device (as in a needle to obtain a blood sample). Obtaining patient information invasively is costly and time consuming. Medical supplies required for patient exams are a physical cost usually incurred by the patient. Invasive exams require the time of medical professionals and patients themselves, time that could be spent tending to other problems. Additionally, invasive testing can be physically and emotionally taxing on the patients themselves, the exam sometimes resulting in needed "recovery time" before treatment can begin. There are also instances where there is a need for continuous monitoring during assessment, treatment, and recovery in which repeated invasive procedures can be problematic to a patient and the healthcare professionals treating the patient.

Blood viscosity is one measurement currently obtained invasively via a blood sample, and can be defined as Lowe [1] states as the intrinsic resistance to blood flow due to internal friction arising between blood's molecular and particulate components. The viscosity of any fluid (measured in millipascals·seconds) is a function of its sheer stress (force per unit area applied to a fluid layer producing this layer's movement relative to an adjacent fluid layer) and its sheer rate (velocity gradient between two adjacent fluid layers), defined by the following equation:

$$(\text{dynamic viscosity})\eta(\text{mPa} \cdot s) = \frac{\text{shear stress (mPa)}}{\text{shear rate }(s^{-1})} \quad (1)$$

Figure 1:
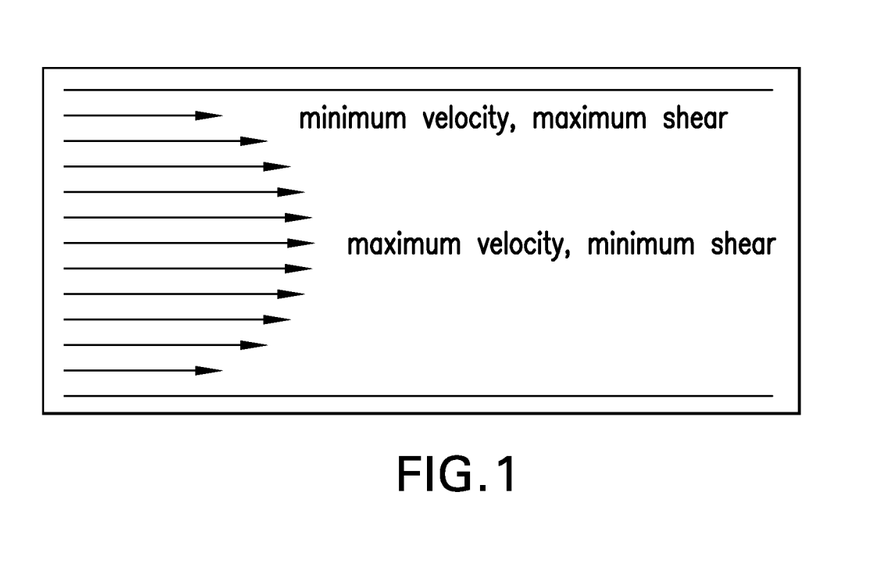
FIG. 1 depicts an illustrative embodiment of a generalized fluid flow.

A pictorial representation of fluid flow in a tube is shown in FIG. 1. FIG. 1 illustrates a parabolic velocity profile (arrows). At the inner walls of the tube, fluid flow has a high shear rate and low velocity, while as you approach the center of the tube, fluid flow has a low shear rate and high velocity. Of the factors influencing blood viscosity, the major contributors include blood plasma, plasma proteins, and both leukocyte and erythrocyte volume (hematocrit), shape, and aggregation [1]. The classic blood viscosity measurement at its simplest involves taking a blood sample, applying a driving pressure through a capillary tube, and measuring the blood's flow rate [1]. By separating whole blood into various components, individual viscosity parameters (i.e., plasma, red blood cell or RBC aggregation, RBC deformability, etc.) can be evaluated.

Blood viscosity variations in erythrocytic factors are indicative of various human ailments, examples including sickle cell disease, red cell membrane defects, and polycythemia [2]. The two major components of RBCs resulting in abnormal viscosity measurements are individual RBC deformation and collective RBC aggregation [3, 4]. Compared to other components of blood, the RBC component is a magnetic material, whose orientation has been shown to be affected by external magnetic fields [5, 6, 7]. The magnetic force felt by erythrocytes depending on there magnetic state can be approximated by the following equation:

$$F_{BC} = \frac{1}{2}\mu_o X V_{BC} \nabla(H \circ H) \quad (2)$$

where $\mu_o$ is the permeability of free space, X is the is the difference in magnetic susceptibility between blood cell and buffer solution (mainly plasma and white blood cells), V is the volume of the blood cell, and H is the applied magnetic field [5]. Additionally, the orientation of an erythrocyte in an external magnetic field is dependent on the oxygenation state of the RBC's hemoglobin, the iron-containing oxygen-carrying component of RBCs [5, 6, 8]. In its oxygenated state, hemoglobin acts as a diamagnetic particle, and in its deoxygenated state, hemoglobin acts as a paramagnetic particle [5, 6]. These differing erythrocytes with magnetic susceptibilities can show that blood oxygenation affects the orientation and aggregation of flowing erythrocytes under a magnetic field, and thus, affects blood viscosity [6].

Pulse oximetry's scientific principle involves differing wavelengths of light having differing degrees of absorption in human tissue. Absorbances of wavelengths of light by a variety of body tissues remain fixed over short periods of time, with an exception in arterial blood flow, which is pulsatile. These constant absorbances (consisting of skin, tissue, cartilage, bone, and venous blood) provide a baseline signal. Pulsatile arterial blood, on the other hand, provides a continuously changing absorbance, which is the signal of interest in pulse oximetry.

Figure 2:
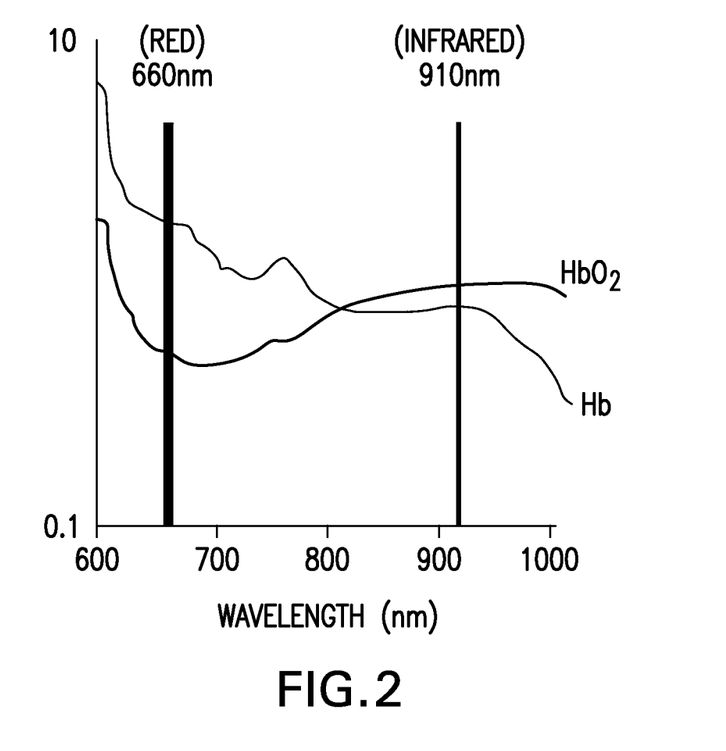
FIG. 2 depicts an illustrative embodiment of a relative absorption of light in hemaglobin.
Figure 3:
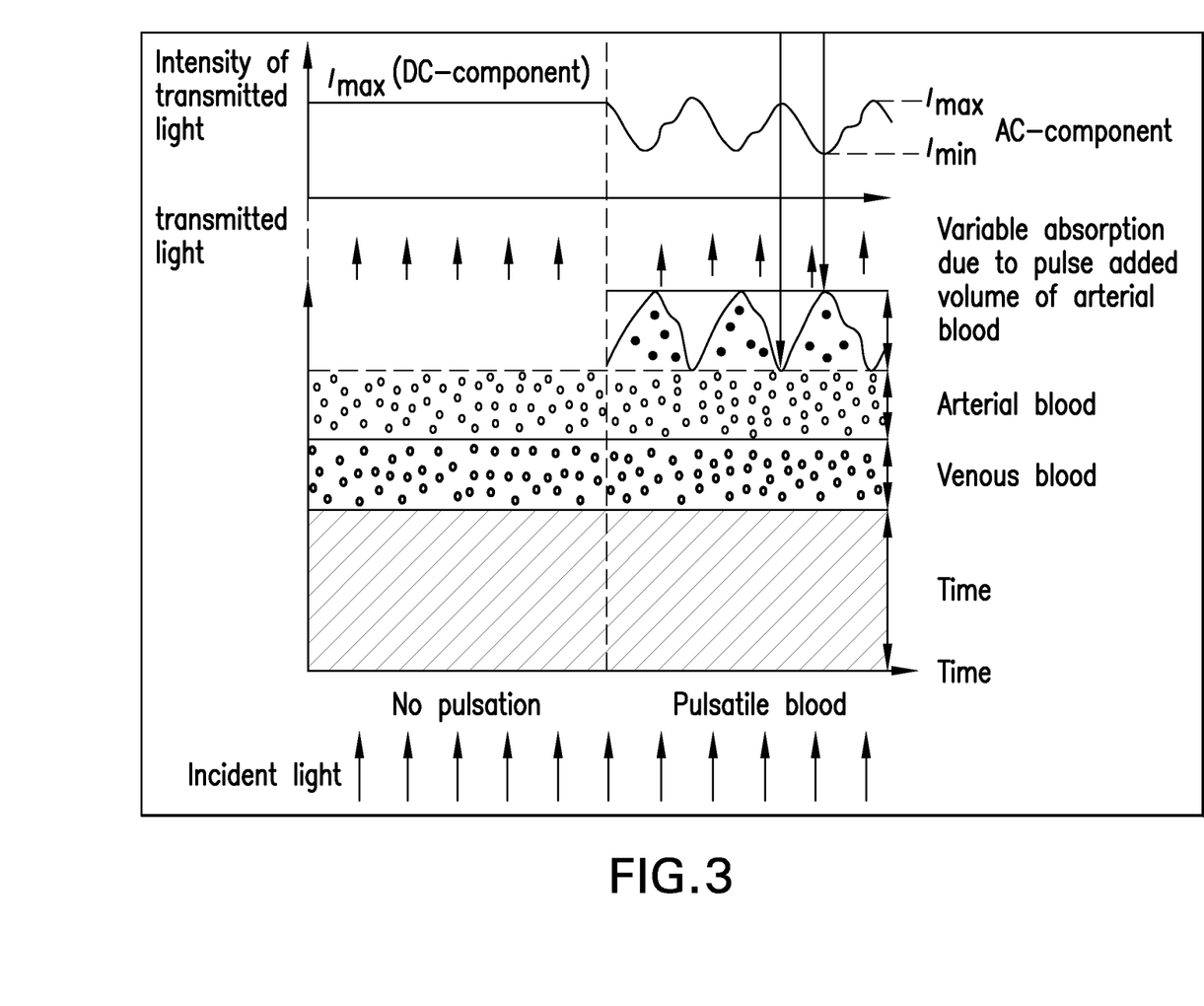
FIG. 3 depicts an illustrative embodiment of pulsatile versus non-pulsatile signals.

The arterial blood has oxygenated and deoxygenated states. The oxygenated state refers to oxygen bound to hemoglobin of erythrocytes ($HbO_2$) and deoxygenated state having hemoglobin lacking oxygen (Hb). Pulse oximetry uses two wavelengths of light, near-infrared light (940 nm) and red light (660 nm). These wavelengths are used because $HbO_2$ and Hb absorbance differs greatly at these wavelengths, with $HbO_2$ absorbing more near-infrared light and allowing more red light to pass, and Hb absorbing more red light and allowing more infrared light to pass. This difference allows a measurement of how oxygenated arterial blood is [9, 10]. An illustration of relative absorbance of Hb and $HbO_2$ is shown in FIG. 2 at various wavelengths of light, with two wavelengths used for pulse oximetry highlighted [9]. FIG. 3 shows the differences in the pulsatile arterial blood with the background signals [10]. The left portion of the graph shows the non-pulsatile signal corresponding to tissues and venous blood flow. This is the DC component of the pulse oximeter signal. The pulsatile arterial blood presents a signal of interest shown on the right of the graph.

A change occurs in a pulse oximeter waveform due to an applied magnetic field based on the degree of blood-oxygen saturation. A blood-oxygen-dependent blood viscosity increase due to a static magnetic field (1.5 T) has been found by Toru Yamamoto [6]. It has also been found that aggregation induced light scattering can occur at the heart's frequency [11]. This aggregation, in turn, has been stimulated by homogenous magnetic fields [12].

Figure 4:
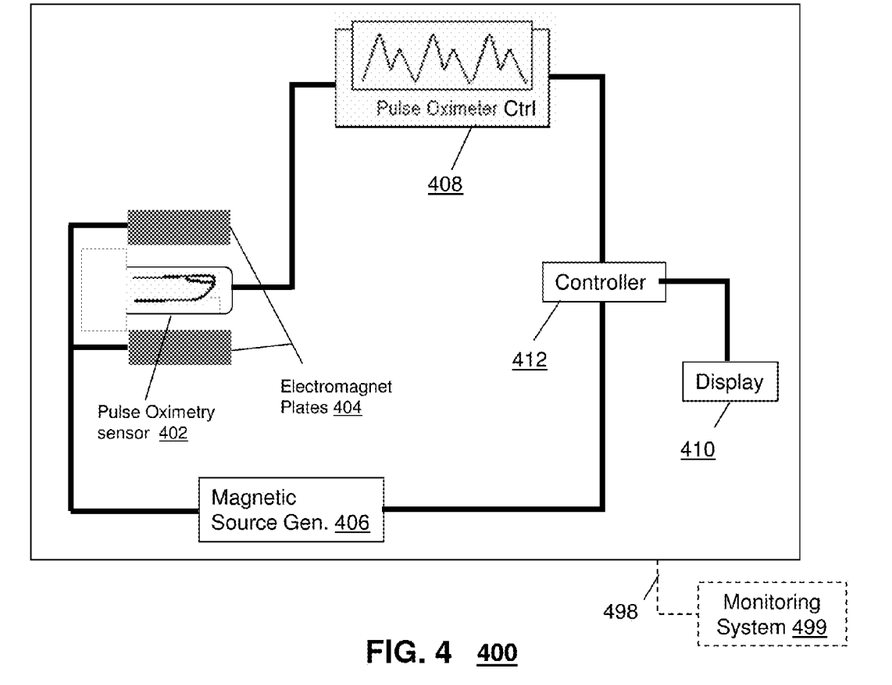
FIG. 4 depicts an illustrative embodiment of a system for measuring an effect on a composition reactive to magnetic fields.

FIG. 4 depicts an illustrative embodiment of a system for measuring an effect on a composition reactive to magnetic fields. In the present illustration the composition is a non-invasive measurement of blood. The system consists of two common electromagnetic plates 404 (such as those produced by Herbach and Rademan™—model no. MA-014) centered about a pulse oximeter sensor 402. The electromagnet plates 404 can be controlled by a common magnetic source generator 406 (such as a common variably-controlled power supply), which controls the magnetic field applied on the pulse oximeter sensor 402.

Figure 5:
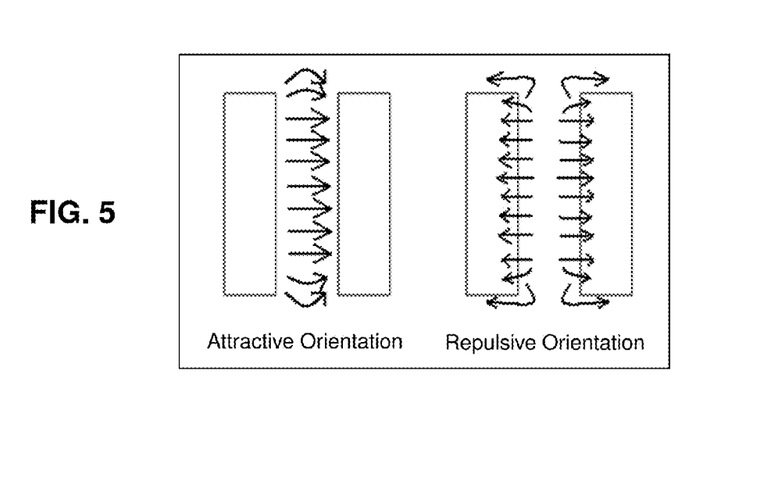
FIG. 5 depicts an illustrative embodiments for orienting magnetic fields between electromagnets of the system of FIG. 4.

The magnetic source generator 406 can control a number of variable aspects of the magnetic field applied by the electromagnet plates 404 including but not limited to amplitude, field duration, magnetic flux, and time and/or frequency control of the magnetic field. Other possible variants for controlling the application of a magnetic field are contemplated by the present disclosure. The magnetic field applied by the electromagnet plates 404 can be symmetric, and can be applied as an attractive or repulsive field as shown in FIG. 5. In another illustrative embodiment, the electromagnet plates 404 can be asymmetric in design, in which case asymmetric magnetic fields can also be applied.

The pulse oximeter sensor 402 can be controlled by a common pulse oximeter controller 408 (such as a Masimo™ Rad-9 Pulse Oximeter), which controls the application of light to an appendage under test (in this case a finger). The pulse oximeter sensor 402 can also have a common light sensor for detecting the absorption of infrared or red light.

A common controller 412 such as a laptop computer, a desktop computer, a micro-controller or other suitable computing devices can be coupled by common means to the pulse oximeter controller 408 and the magnetic source generator 406 to control their operation and to process measurements supplied by the pulse oximeter controller 408. The controller 412 can present its results on a common display 410 (e.g., an LCD monitor). The results can be a combination of waveforms and textual messages listing for example statistics, diagnostic information, and/or a prognosis.

Figure 6:
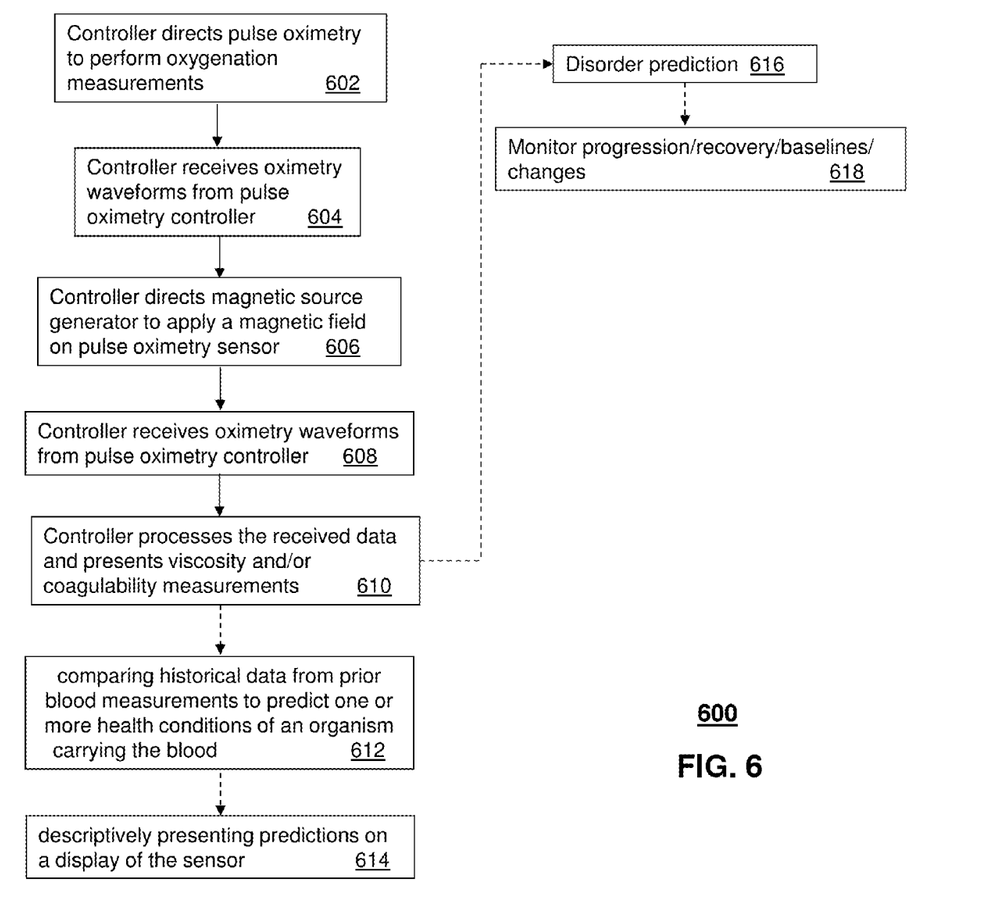
FIG. 6 depicts an illustrative method operating in the system of FIG. 5.

FIG. 6 depicts an illustrative method 600 operating in the system of FIG. 4. Method 600 begins with step 602 in which the controller 412 directs the pulse oximeter controller 408 to perform oxygenation measurements as is commonly performed by such sensors. The controller 412 can utilize the measurements supplied in step 604 by the pulse oximeter controller 408 to establish a baseline for oxygenation measurements unaffected by a magnetic field. Once a baseline has been established, the controller 412 can direct in step 606 the magnetic source generator to apply a magnetic field on the pulse oximeter sensor 402. The magnetic field can be applied while the pulse oximeter controller 408 is performing measurements, or while it is in standby mode (i.e., without applying light or performing light absorption measurements).

As noted earlier, the magnetic field can be applied in varied forms. For example, the amplitude of the magnetic field can vary in time, the magnetic flux can be symmetric or asymmetric, the direction of the flux can be of opposing or attracting fields, and so on. The variability of the magnetic field can be used to affect the flow and/or aggregation of blood cells in a variety of ways which can be correlated to viscosity and/or coagulability measurements. In step 608, the controller 412 can receive the oximetry waveforms from the pulse oximeter controller 408, which it then processes in step 610. The controller 412 can for example compare a change between the baseline amplitude, phase, waveform shape, and/or slope of the pulse oximetry waveforms supplied in step 604 to the waveforms supplied in step 608. The changes detected in these metrics singly or in combination can be used to determine viscosity of the blood in the appendage and/or a probability of coagulability. From these comparisons it may also be possible to non-invasively measure a Prothrombin Time (PT), a Partial Thromboplastin Time (PTT), and/or an International Normalized Ratio (INR). The controller 412 can compare historical data from prior blood measurements to predict on or more health conditions of an organism carrying the blood as in step 612, and can descriptively present the predictions on a display of the sensor as in step 614. The method can also include predicting a likelihood of one or more disorders from the measurement at 616; and performing monitoring at 618 including monitoring disease progression, monitoring recovery, monitoring baseline levels of an organism from which the plurality of biological cells originate, and/or monitoring changes before and after administration of a treatment applied to the organism. The one or more disorders can include at least one of a variant of anemia, a variant of cancer, a variant of kidney disease, hemochromatosis, polycythemias, sickle cell disease, thalasemias, coagulapathies, a hydration disorder, disseminated intravascular coagulation (DIC), or combinations thereof. The method can operate in a portable sensing device (as illustrated by the square outline), where the portable sensing device is communicatively coupled to a monitoring system 499 by the wireline or wireless means 498 as shown in FIG. 4. The monitoring system 499 can correspond to at least one of an intensive care monitoring unit, a patient record system, or a doctor alerting system.

Method 600 can be cycled a number of times to statistically assess a confidence level in the measurements performed. Moreover, historical measurements can be utilized to detect deterioration or improvement in a patient's condition as medication is applied over the course of treatment. Method 600 and system 400 of FIG. 4 can be utilized by hospital personnel or by the patient while at the patient's residence. System 400 can be utilize to diagnose disorders such as a variant of anemia, a variant of cancer, a variant of kidney disease, hemochromatosis, polycythemias, sickle cell disease, thalasemias, coagulapathies, a hydration disorder, and disseminated intravascular coagulation (DIC).

From the foregoing descriptions, it would be evident to an artisan with ordinary skill in the art that the aforementioned embodiments can be modified, reduced, or enhanced without departing from the scope and spirit of the claims described below. For example, method 600 can be adapted so that measurements supplied by the pulse oximeter controller 408 are based on discrete digital sampling rather than analog waveforms. Method 600 can also be adapted so that the controller 412 can present a diagnosis and/or prognosis for a patient undergoing measurements. In yet another illustrative embodiment, method 600 can be used non-invasively on any organism to measure liquid viscosity and/or coagulability of said liquid.

In another embodiment, the pulse oximeter sensor 402 can be applied to other portions of a patient such as a portion of an arm, a portion of a leg, a portion of a neck, a portion of an ear, a portion of a forehead, a portion of a hand, and a portion of a foot. In yet another embodiment, the electromagnetic plates 404 can be replaced with an electromagnetic ring coaxially placed over the pulse oximeter sensor 402. In another embodiment, the magnetic source generator 406 can vary the magnetic field of each magnetic plate 404 independently or contemporaneously. The magnetic fields created by each plate 404 can be static magnetic fields or time-dependent magnetic fields.

Generally speaking, the system of FIG. 4 can be applied to any composition which has particulates that are kinetically reactive to a magnetic field and from which characteristics of the composition can be correlated to the absorption and/or scattering of a portion of a spectrum of light applied on said composition before, after, or during the application of a magnetic field on the composition.

It would be evident to an artisan of ordinary skill in the art from the above embodiments that other suitable modifications can be applied to the present disclosure. Accordingly, the reader is directed to the claims for a fuller understanding of the breadth and scope of the present disclosure.

Figure 7:
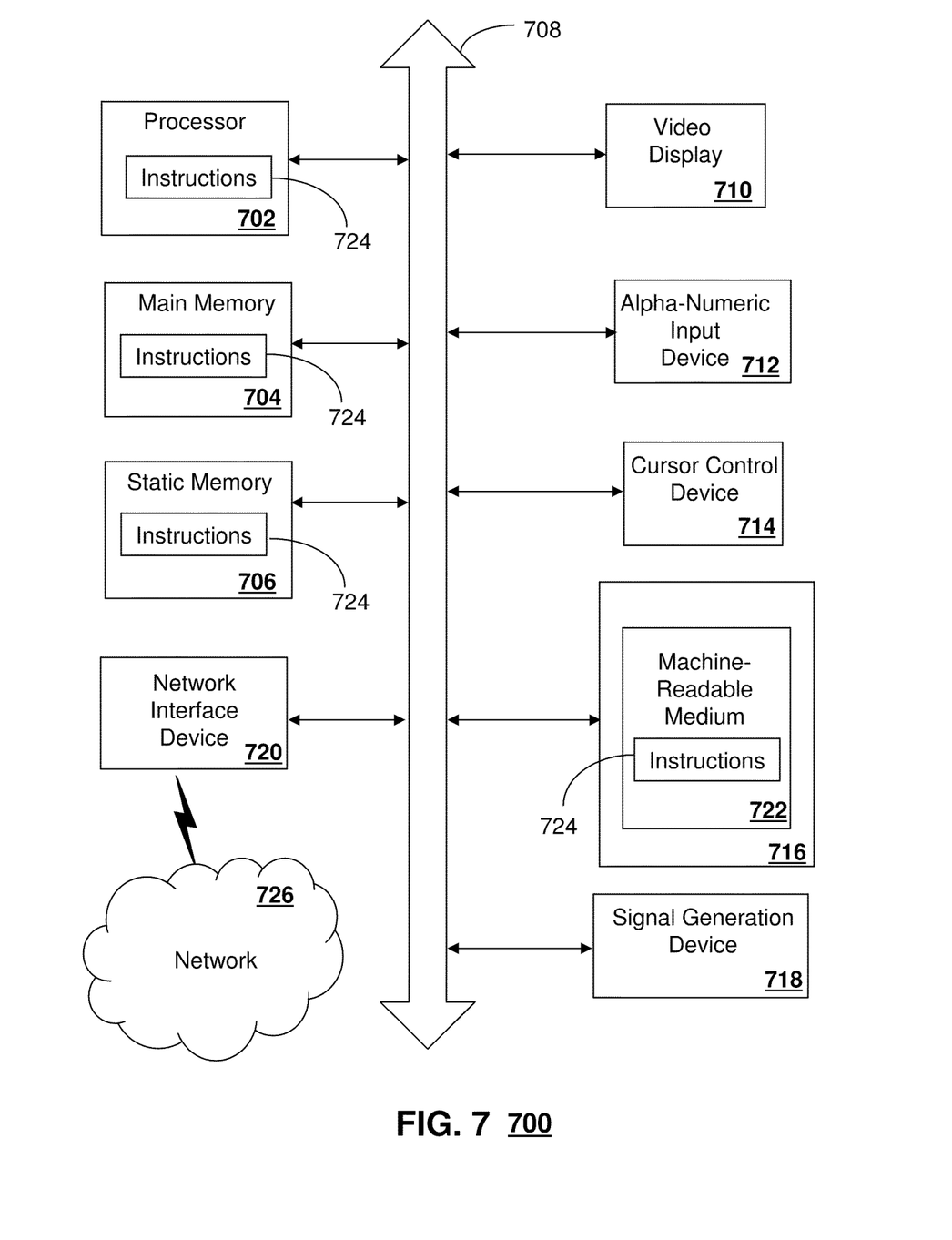
FIG. 7 depicts an illustrative diagrammatic representation of a machine in the form of a computer system within which a set of instructions, when executed, may cause the machine to perform any one or more of the methodologies disclosed herein.

FIG. 7 depicts an illustrative diagrammatic representation of a machine in the form of a computer system 700 within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

The computer system 700 may include a processor 702 (e.g., a central processing unit (CPU), a graphics processing unit (GPU, or both), a main memory 704 and a static memory 706, which communicate with each other via a bus 708. The computer system 700 may further include a video display unit 710 (e.g., a liquid crystal display (LCD), a flat panel, a solid state display, or a cathode ray tube (CRT)). The computer system 700 may include an input device 712 (e.g., a keyboard), a cursor control device 714 (e.g., a mouse), a disk drive unit 716, a signal generation device 718 (e.g., a speaker or remote control) and a network interface device 720.

The disk drive unit 716 may include a machine-readable medium 722 on which is stored one or more sets of instructions (e.g., software 724) embodying any one or more of the methodologies or functions described herein, including those methods illustrated above. The instructions 724 may also reside, completely or at least partially, within the main memory 704, the static memory 706, and/or within the processor 702 during execution thereof by the computer system 700. The main memory 704 and the processor 702 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 724, or that which receives and executes instructions 724 from a propagated signal so that a device connected to a network environment 726 can send or receive voice, video or data, and to communicate over the network 726 using the instructions 724. The instructions 724 may further be transmitted or received over a network 726 via the network interface device 720.

While the machine-readable medium 722 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

REFERENCES

[1] G. D. O. Lowe, "Blood rheology in vitro and in vivo," in *Bailliére's Clinical Haematology*, Bailliere Tindall, Publisher. UK. September 1987, Vol. 1, No. 3 pp. 597-636.

[2] J. Stuart and G. B. Nash, "Red cell deformability and haematological disorders," Blood Reviews. 4, 141-147 (1990).
[3] S. Chien, S. Usami, R. J. Dellenback, M. I. Gregersen, L. B. Nanninga, and M. M. Guest, "Blood viscosity: influence of erythrocyte aggregation," Science, 157, 3790 (1967).
[4] S. Chien, S. Usami, R. J. Dellenback, and M. I. Gregersen, "Blood viscosity: influence of erythrocyte deformation," Science, 157, 3790 (1967).
[5] K. Han, and A. B. Frazier, "Continuous magnetophoretic separation of blood cells in microdevice format," J. Appl. Phys. 96, 10 (2004).
[6] T. Yamamoto, Y Nagayama, and M. Tamura, "A blood-oxygenation-dependent increase in blood viscosity due to a static magnetic field," Phys. Med. Biol. 49 (2004).
[7] T. Higashi, A. Yamagishi, T. Takeuchi, N. Kawaguchi, S. Sagawa, S. Onishi, and M. Date, "Orientation of erythrocytes in a strong static magnetic field," Blood 82, 4 (1993).
[8] M. Okazaki, N. Maeda, and T. Shiga, "Effects of an inhomogeneous magnetic field on flowing erythrocytes," Eur Biophys J 14 (1987).
[9] S. J. Barker, B. Hay, K. Miyasaka, and C. Poets, "Principles of pulse oximetry technology," September 2002, http://oximetry.org/pulseox/principles.htm.
[10] R. S. Khandpur, *Biomedical Instrumentation: Technology and Applications*. Chicago: McGraw-Hill, 2005, pp. 318-322.
[11] L. D. Shvartsman and I. Fine, "Optical transmission of blood: effect of erythrocyte aggregation," IEEE Transactions on Biomedical Engineering 50, 8 (2003).
[12] M. Iino, "Effects of a homogenous magnetic field on erythrocyte sedimentation and aggregation," Bioelectromagnetics 18 (1997).

What is claimed is:

1. A sensor, comprising:
a pulse oximeter sensor to measure an oxygen saturation level in a liquid;
a magnetic source coupled to the pulse oximeter sensor, wherein the magnetic source comprises an electromagnetic element having an electromagnetic ring placed coaxially over the pulse oximeter sensor;
a memory storing computer instructions, wherein the memory is a non-transitory memory device; and
a controller coupled to the pulse oximeter sensor, the magnetic source, and the memory, wherein responsive to executing the computer instructions the controller performs operations comprising:
controlling the pulse oximeter sensor and the magnetic source, and
measuring a mechanical effect on the liquid responsive to the magnetic source applying a magnetic field to the liquid.

2. The sensor of claim 1, wherein the liquid comprises blood, and wherein the mechanical effect correlates to at least one of a viscosity level of the blood, a coagulability of the blood, or both.

3. The sensor of claim 1, wherein the pulse oximeter sensor and the magnetic source are adapted to be coupled to a portion of an organism to perform measurements on the liquid carried by said portion.

4. The sensor of claim 3, wherein the organism corresponds to a human, and wherein the portion of the human comprises one of at least a portion of an arm, a portion of a leg, a portion of a neck, a portion of an ear, a portion of a forehead, a portion of a hand, or a portion of a foot.

5. The sensor of claim 1, wherein the electromagnetic element is coupled to a signal generator controlled by the controller.

6. The sensor of claim 5, wherein the magnetic field is a time-dependent magnetic field.

7. The sensor of claim 5, wherein the signal generator controls aspects of the magnetic field, and wherein the aspects controlled include at least one of an intensity of the magnetic field, a duration of the magnetic field, a gradient of the magnetic field, a flux of the magnetic field, an orientation of the magnetic field, a direction of the magnetic field, a modulation of the magnetic field, or a time-dependent change of the magnetic field.

8. The sensor of claim 6, wherein the signal generator controls a plurality of electromagnetic devices independently or contemporaneously.

9. The sensor of claim 2, wherein signals supplied to the controller by the pulse oximeter sensor are affected by an application of the magnetic field on the blood.

10. The sensor of claim 9, wherein signals supplied to the controller by the pulse oximeter sensor correlate to at least one of a viscosity level of the blood, a coagulability of the blood, or both.

11. The sensor of claim 9, wherein responsive to executing the computer instructions, the controller further performs the operation of presenting a graphical user interface according to the signals supplied by the pulse oximeter sensor.

12. The sensor of claim 10, wherein responsive to executing the computer instructions, the controller further performs the operation of measuring one or more characteristics of the blood from a comparison of signals supplied by the pulse oximeter sensor before, during, or after an application of the magnetic field on the blood.

13. The sensor of claim 12, wherein responsive to executing the computer instructions, the controller further performs the operation of measuring the one or more characteristics of the blood from at least one of an amplitude, slope, waveform change, or phase shift of the signals supplied by the pulse oximeter sensor.

14. The sensor of claim 12, wherein the one or more characteristics of the blood correspond to at least one of a viscosity level of the blood, a coagulability of the blood, or both.

15. The sensor of claim 14, wherein responsive to executing the computer instructions the controller performs operations comprising determining at least one of an accumulation level of an iron concentration in the blood according to an amplitude of the signals supplied by the pulse oximeter sensor.

16. The sensor of claim 15, wherein a change in amplitude of the signals supplied by the pulse oximeter sensor corresponds to a change in one of an accumulation of blood or the iron concentration in the blood.

17. The sensor of claim 14, wherein responsive to executing the computer instructions, the controller further performs the operation of determining at least one of the viscosity level and coagulability of the blood according to at least one of a slope, a waveform change, an amplitude, or a phase shift of the signals supplied by the pulse oximeter sensor.

18. The sensor of claim 17, wherein a change in at least one of the slope, the amplitude, the phase, or a waveform shape in a portion of the signals supplied by the pulse oximeter sensor corresponds to at least one of a change in the viscosity of the blood or a change in a probability that the blood will coagulate.

19. The sensor of claim 1, wherein the pulse oximeter sensor performs time-dependent measurements, and wherein the magnetic field is one of a static magnetic field or a time-dependent magnetic field.

20. The sensor of claim 14, wherein responsive to executing the computer instructions, the controller further performs the operation of presenting on a display one or more indicators corresponding to at least one of the viscosity level of the blood, the coagulability of the blood, or both.

21. The sensor of claim 20, wherein the one or more indicators correspond to at least one of one or more numerical metrics, one or more waveform plots, or one or more descriptive diagnostics.

22. The sensor of claim 14, wherein responsive to executing the computer instructions, the controller further performs the operation of:
comparing historical data from prior blood measurements to predict one or more health conditions of an organism carrying the blood; and
descriptively presenting said predictions on a display of the sensor.

23. A method, comprising:
applying, by a device with at least one processor and opposing magnetic plates, a magnetic field on a plurality of biological cells carrying oxygen and one or more particles that kinetically react to magnetic fields, wherein the plurality of biological cells are positionable between the opposing electromagnetic plates; and
measuring, by the device, a mechanical effect from the application of the magnetic field on at least a portion of the plurality of biological cells according to a change in an oxygen saturation level of said portion of the plurality of biological cells.

24. The method of claim 23, wherein the plurality of cells comprise one of erythrocyte cells or tissue cells.

25. The method of claim 24, comprising at least one of:
predicting, by the device, a likelihood of one or more disorders from the measurement;
monitoring, by the device, disease progression;
monitoring, by the device, recovery;
monitoring, by the device, baseline levels of an organism from which the plurality of biological cells originate; or
monitoring, by the device, changes before and after administration of a treatment applied to the organism.

26. The method of claim 25, wherein the one or more disorders comprise at least one of a variant of anemia, a variant of cancer, a variant of kidney disease, hemochromatosis, polycythemias, sickle cell disease, thalasemias, coagulapathies, a hydration disorder, disseminated intravascular coagulation (DIC).

27. The method of claim 23, wherein the method operates in a portable sensing device, and wherein the portable sensing device is communicatively coupled to a monitoring system by wireline or wireless means.

28. The method of claim 27, wherein the monitoring system corresponds to at least one of an intensive care monitoring unit, a patient record system, or a doctor alerting system.

29. A method, comprising:
non-invasively applying, by a device with at least one processor and a magnetic applicator, a magnetic field on a portion of a living organism, wherein the portion is positionable in proximity to the magnetic applicator, wherein the magnetic applicator comprises opposing magnetic plates, and wherein changes in absorption or scattering of a select spectrum of light correlate to at least one of a viscosity of a liquid in the living organism, a coagulability of said liquid, or a combination thereof; and
non-invasively measuring, by the device, changes from the application of the magnetic field in at east one of an absorption or scattering of a select spectrum of light applied on the living organism.

30. A method, comprising:
non-invasively applying, by a device with at least one processor and a magnetic applicator, a magnetic field on a portion of a living organism, wherein the portion is positionable in proximity to the magnetic applicator, wherein the magnetic applicator comprises a coil, and wherein a liquid in the living organism comprises blood, and wherein changes in absorption or scattering of a select spectrum of light corresponds to a change in an oxygen saturation level of the blood; and
non-invasively measuring, by the device, changes from the application of the magnetic field in at least one of an absorption or scattering of the select spectrum of light applied on the living organism.

31. A sensor, comprising:
a pulse oximeter sensor to measure an oxygen saturation level in a liquid;
a magnetic source coupled to the pulse oximeter sensor, wherein the magnetic source comprises opposing electromagnetic plates partially surrounding the pulse oximeter sensor;
a memory storing computer instructions, wherein the memory is a non-transitory memory device; and
a controller coupled to the pulse oximeter sensor, the magnetic source, and the memory, wherein responsive to executing the computer instructions the controller performs operations comprising:
controlling the pulse oximeter sensor and the magnetic source, and
measuring a mechanical effect on the liquid responsive to the magnetic source applying a magnetic field to the liquid.

32. The sensor of claim 31, wherein the magnetic field is asymmetrical.

* * * * *